United States Patent [19]

Rantala

[11] Patent Number: 4,595,018
[45] Date of Patent: Jun. 17, 1986

[54] METHOD OF FURTHER DEVELOPING THE MEASURING OF A NEURO-MUSCULAR JUNCTION

[75] Inventor: Börje Rantala, Helsinki, Finland

[73] Assignee: Instrumentarium Corp., Finland

[21] Appl. No.: 617,936

[22] Filed: Jun. 6, 1984

[30] Foreign Application Priority Data

Jun. 10, 1983 [FI] Finland ................................ 832091

[51] Int. Cl.$^4$ .............................................. A61B 5/05
[52] U.S. Cl. ..................................... 128/733; 128/741
[58] Field of Search ......................... 128/733, 741, 783

[56] References Cited

U.S. PATENT DOCUMENTS

| | | | |
|---|---|---|---|
| 3,364,929 | 1/1968 | Ide et al. ........................ | 128/733 X |
| 3,905,355 | 9/1975 | Brudny .............................. | 128/733 |
| 3,916,876 | 11/1975 | Freeman ............................ | 128/733 |
| 4,148,303 | 4/1979 | Cohen ................................ | 128/733 |
| 4,291,705 | 9/1981 | Severinghaus et al. ............ | 128/733 |
| 4,387,723 | 6/1983 | Atlee et al. ...................... | 128/741 X |

FOREIGN PATENT DOCUMENTS 2457854 12/1975 Fed. Rep. of Germany ...... 128/733

OTHER PUBLICATIONS

Pavlov et al., "Neuromuscular Block Indicator", Biomed. Eng. vol. 13, No. 4, Jul.–Aug., 1979, pp. 205–207.
Kwatny et al., "Appln. of Sig. Proc. Tech. to Study of Myoelectric Signals", IEEE Biomed. Eng. vol. 17, No. 4, Oct./1970, pp. 303–306.

Primary Examiner—Edward M. Coven
Attorney, Agent, or Firm—Andrus, Sceales, Starke & Sawall

[57] ABSTRACT

The invention relates to a method of further developing the measuring of so-called neuromuscular transmission (or NMT), said measuring being effected by stimulating with electric pulses a given muscular nerve, e.g. the ulnar nerve in the arm of a patient, and by measuring a corresponding muscular block by means of EMG. In the prior art NMT-measurings, a stimulus artefact, caused by stimulation and induced directly electrically and independently of a stimulus passing through said muscular nerve, may often distort measuring results. According to the invention, this artefact is not tried to be eliminated by various gate solutions but, instead, it is measured by first effecting a measurement prior to the actual neuromuscular block measurements e.g. in connection with the calibration of the control or reference value of a muscular block and by recording or storing this first value of a stimulus artefact. This is followed by monitoring the changes of stimulus artefact values by measuring said stimulus artefact during the measurements of a neuromuscular junction and by comparing the thus obtained stimulus artefact values with said first value, not only for securing the reliability of measuring information but also preferably for controlling the state variations and condition of NMT-measuring instruments. By digitizing the collected information, the measuring errors can be preferably eliminated mathematically by utilizing data processing.

2 Claims, 3 Drawing Figures

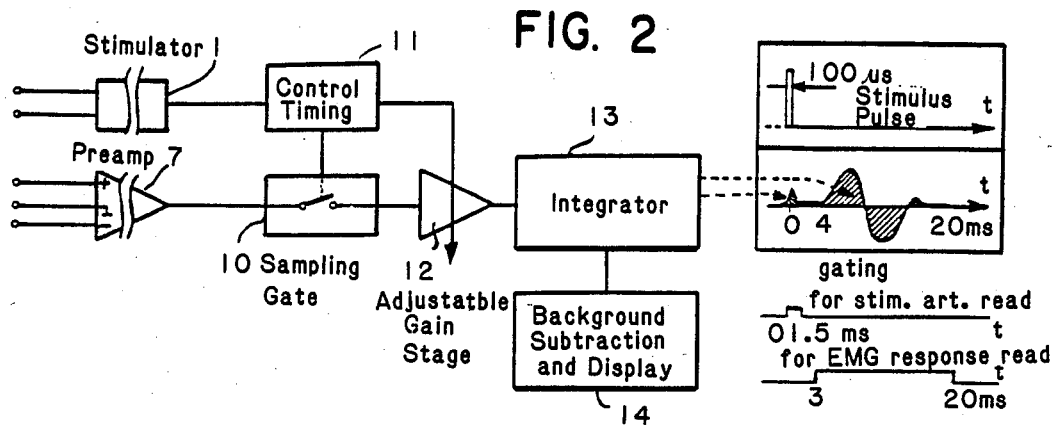
FIG. 2
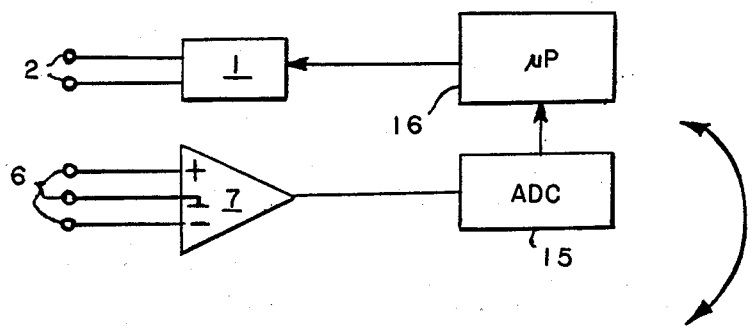
FIG. 3
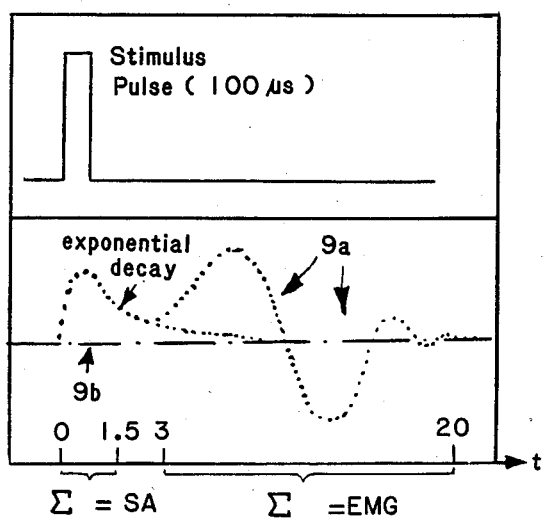

METHOD OF FURTHER DEVELOPING THE MEASURING OF A NEURO-MUSCULAR JUNCTION

The present invention relates to a method of further developing the measuring of neuromuscular transmission (or NMT), wherein said measuring is effected by stimulating with electric pulses some muscular nerve, e.g. the ulnar nerve in the arm of a patient, and by measuring the corresponding muscular block by means of EMG.

BACKGROUND OF THE INVENTION

One problem in the above-described NMT-measuring is that the final measuring result is affected by a rather large number of factors, including a stimulation electrode junction, a path from dermal surface to nerve, a neuromuscular junction forming the actual target to be examined, the electric acitivity of a muscle, a path from muscle to dermal surface, the EMG-electrode junction. In particular, the electrode set-up and the fastening and state of electrodes may lead to errors in a measuring result, which are difficult to detect and/or whose effect on a measuring result is difficult to observe.

The electrical stimulation itself results in a certain additional block, a so-called stimulus artefact (or S.A.), which is the part of a stimulus not passing via the nerve-neuromuscular junction-muscle route but, instead, is electrically conducted directly from stimulus electrode junction to EMG-electrode junction. Since this direct electrical conductance proceeds faster than the passage of a stimulus through a nerve, the block caused by stimulus artefact appears in measuring results respectively prior to the actual muscular blcok caused by stimulation. Thus, in the prior art NMT-measuring methods, a stimulus artefact has been tried to be eliminated by using gate circuits in a manner that the block signal is mainly recorded only during the actual muscular block (see e.g. the article H.S. Lam, N.M. Cass, K.C. Ng, Electromyographic monitoring of neuromuscular block, Br. J. Anaesth. (1981), 53, 1351). In practice, however, a stimulus artefact and an actual muscular block may be partially overlapped, whereby such procedure is of no help but the measuring results will be distorted.

SUMMARY OF THE INVENTION

An object of the invention is to eliminate the above deficiencies of the prior art NMT-measuring methods, to improve the reliability of measuring results and to facilitate the monitoring possibilities of such an examination apparatus in order to eliminate the systematic measuring errors caused by such apparatus.

The objects of the invention are achieved as set forth in more detail in the characterizing section of claim 1 and in subclaims. Thus, characteristic of the invention is that the aim is not to eliminate a stimulus artefact as such but, instead, whenever it occurs in such a degree that measuring results may be substantially distorted, said stimulus artefact will in fact be measured and its effect on and share of a measuring block will be determined in order to find out the actual muscular block.

By monitoring, according to the invention, a stimulus artefact block and by comparing it with the original value, it is possible to draw conclusions about the state of measuring instruments and, thus, about the possible systematic errors caused in measuring results by changes. This is particularly significant in surgical operations, wherein NMT-measuring and monitoring are utilized when controlling the effect of paralyzing substances acting on a neuromuscular junction of a patient, since, following the positioning and calibration of measuring instruments, it is not generally possible to continuously monitor the state of the instrumental assembly. Thus, for example, the sudden disappearance of EMG-block and stimulus artefact does not indicate paralysis of a patient but, instead, damage of detachment of an electrode, cables, amplifiers or the like, since a stimulus artefact is generated despite the activity of paralyzing agents.

On one hand, the invention can be applied to monitor the condition of measuring instruments and the proper order of the assembly in an actual measuring event by monitoring the changes of a stimulus artefact as such. On the other hand, it is possible to detect and quantify a possibly disturbing action of a stimulus artefact, e.g. a possible overlapping with an actual muscular block, and such action can be further taken into consideration e.g. mathematically.

DESCRIPTION OF THE DRAWINGS

The invention will now be described in more detail with reference made to the accompanying drawing, in which FIG. 2 shows diagrammatically a measuring system for applying the invention, FIG. 3 shows diagrammatically another measuring system for applying the invention.

DESCRIPTION OF THE ILLUSTRATED EMBODIMENT

Figure 1:
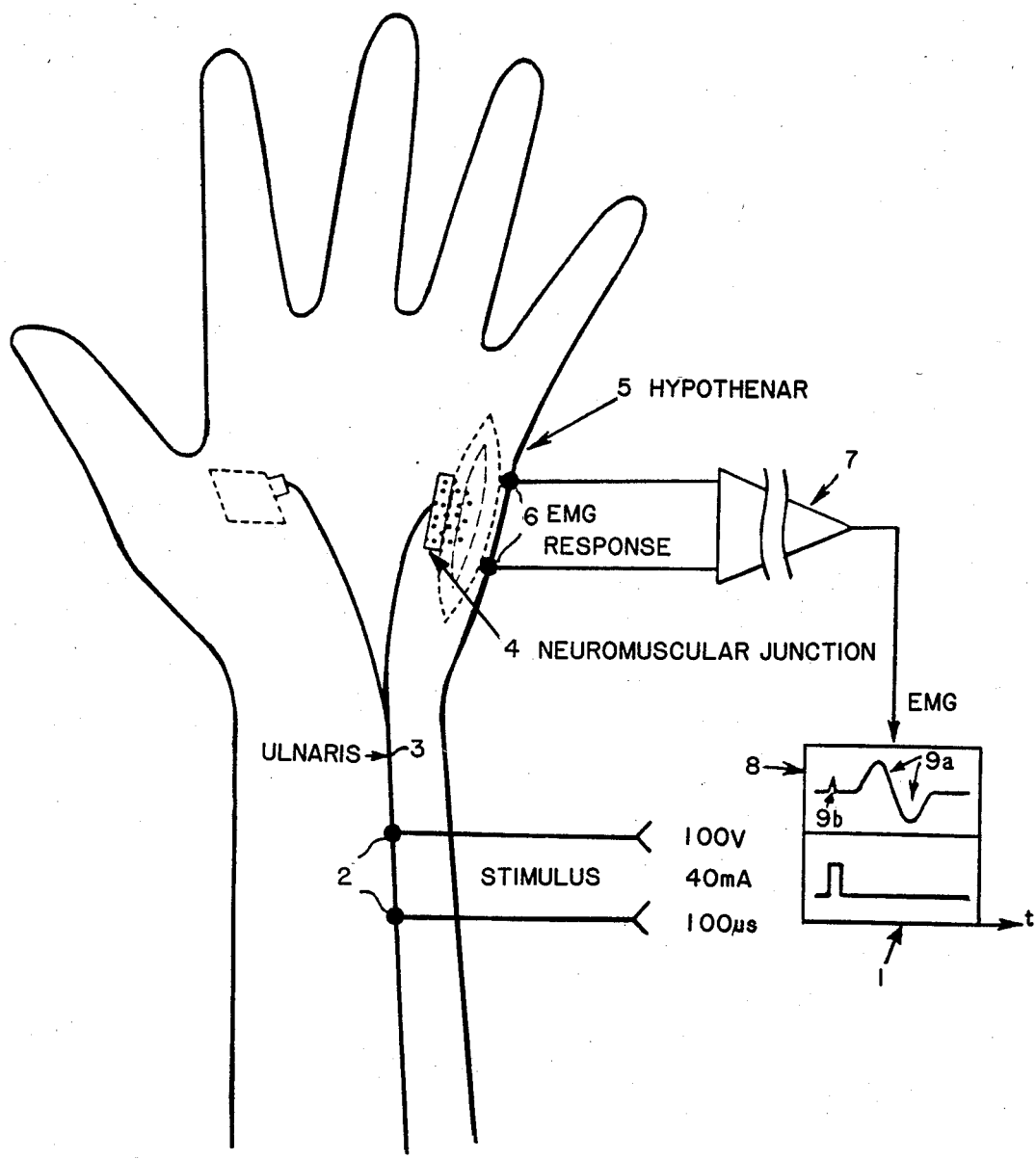
FIG. 1 shows the principle of neuromuscular junction or NMT-measuring.

Referring to the drawing and especially to FIG. 1 thereof, NMT-measuring is typically effected in a manner that a nerve stimulator 1 is used to issue electric pulses through electrodes 2 to a muscular nerve, in this example the ulnaris nerve. To stimulus proceeds along the nerve to a neuromuscular junction 4. The block caused by said stimulus in a muscle 5 (in this case hypothenar) is measured by means of EMG-electrodes 6, gained 7, and information 8 is processed for display. Regardless of a stimulus passing through a nerve, the stimulation also results in a directly electrically conducting block or a stimulus artefact 9b to EMG-electrodes, said artefact being detected and displayed prior to an actual muscular block 9a. As for the general principles and applications of NMT-measuring, reference is also made to the above-cited reference article.

A measuring system shown in FIG. 2 comprises, in addition to a stimulator 1 and a preamplifier 7, a sampling gate 10 and control and timing means for carrying out the measuring separately for a stimulus artefact and a muscular block, as well as an adjustable gain stage 12. The apparatus configuration further comprises an integrator 13 for calculating the integrated values of stimulus artefact 9b and muscular block 9a. The information processing means 14 process the collected information for display. In addition, such means effect the storage of a first stimulus artefact value, compare later artefact values with this, and subtract from block values a so-called background response, i.e. a possible block independent of stimulation. If desired, processor 14 can be programmed to give the alarm if a stimulus artefact suddenly disappears or rises substantially.

The configuration of FIG. 2 has first of all a weakness that it is only capable of determining a stimulus artefact and a muscular block alternately, i.e. on different stimulations. This drawback can be overcome by providing said configuration with another gate and another integrator, whereby the blocks can be measured at the same time by one stimulation. This naturally increases the apparatus costs.

Another weakness is that, if a stimulus artefact 9b overlaps with an actual muscular block 9a, this configuration is not capable of separating the stimulus artefact portion of a block apart in order to find out a purely muscular block. In this respect, for example, FIG. 3 shows a more favorable solution, wherein the analogous signals after the preamplification and prior to the information processing 16 are digitized at 15. Thus, a processor 16 can take care of e.g. the timing of stimulation and detection, integration, information storage and comparison, determination of the portion of stimulus artefact overlapping with a muscular block and subtraction thereof from the values of a muscular block prior to the display output, as well as the data processing required by the display itself, all these being performed with conventional programmatic means without the need for accessories. As shown in FIG. 3, the sampling points of the digitized curves are added up from certain distances, e.g. those shown in FIGS. 2 and 3, separately from stimulus artefact 9b and muscular block 9a. When the blocks are overlapping, the share of artefact can be determined mathematically by means of an artefact describing, exponentially decaying function in a manner that the share of artefact is calculated by extrapolation and thus substracted from the measured values of a muscular block.

The method according to the invention can be applied to various stimulation methods as long as the block measuring is effected electrically by means of EMG. Just by way of example, FIG. 1 shows certain values for a stimulation pulse: 100 V, 40 mA, 100 μs.

The principle of this invention is by no means limited to certain muscles and muscular nerves. For example, in actual surgical operations, the arrangement shown in FIG. 1 is quite preferable since, in this case, the measuring instruments generally disturb as little as possible the actual performance of an operation and other monitoring activity. It should be noted, however, that if a stimulus artefact during the calibration of measuring equipment is very low, it will be difficult to draw any conclusions about its disappearance. A reason for this may be e.g. that stimulation electrodes are positioned too far away from the EMG-electrode junction. Also in this respect the arrangement shown in FIG. 1 is preferable and in practice has been found to work properly.

The invention is not limited to the embodiments shown but a plurality of modifications thereof are conceivable within the scope of the annexed claims.

I claim:

1. A method of enhancing the accuracy and reliability of neuromuscular block monitoring, comprising the steps of stimulating with electric pulses a given muscular nerve of a patient, measuring a corresponding muscular block by EMG, measuring a stimulus artefact caused by stimulation induced directly electrically and independently of a stimulus passing through said muscular nerve prior to the actual neuromuscular block, recording the value of stimulus artefact, monitoring changes of stimulus artefact values by measuring said stimulus artefact during measurements of a neuromuscular junction, and comparing the latter obtained stimulus artefact values with said first stimulus artefact values to control the state variations of NMT-measuring instruments and improve the reliability of measuring information.

2. A method as set forth in cliam 1, characterized in that, when a stimulus artefact and a muscular block appear partially simultaneously, the portion of stimulus artefact overlapping with a muscular block is determined and this portion is subtracted from the measured values of a muscular block.

* * * * *